United States Patent
Nuber et al.

(10) Patent No.: US 12,252,677 B2
(45) Date of Patent: Mar. 18, 2025

(54) FLUIDIC DEVICE, FLUIDIC SYSTEM, AND METHOD FOR DEVELOPING THREE-DIMENSIONAL CELLULAR CONSTRUCTIONS

(71) Applicant: TECHNISCHE UNIVERSITÄT DARMSTADT, Darmstadt (DE)

(72) Inventors: Ulrike Nuber, Mühltal (DE); Heinz Koeppl, Darmstadt (DE); Steffen Hardt, Gross-Zimmern (DE); Katrin Töpfer, Darmstadt (DE)

(73) Assignee: TECHNISCHE UNIVERSITÄT DARMSTADT, Darmstadt (DE)

( * ) Notice: Subject to any disclaimer, the term of this patent is extended or adjusted under 35 U.S.C. 154(b) by 1001 days.

(21) Appl. No.: 17/287,749

(22) PCT Filed: Oct. 28, 2019

(86) PCT No.: PCT/EP2019/079418
§ 371 (c)(1),
(2) Date: Apr. 22, 2021

(87) PCT Pub. No.: WO2020/089178
PCT Pub. Date: May 7, 2020

(65) Prior Publication Data
US 2021/0355422 A1    Nov. 18, 2021

(30) Foreign Application Priority Data

Nov. 2, 2018 (DE) .......................... 102018127406.8

(51) Int. Cl.
*C12M 3/06* (2006.01)
*C12M 1/00* (2006.01)
*C12M 3/00* (2006.01)

(52) U.S. Cl.
CPC ............ *C12M 23/16* (2013.01); *C12M 21/08* (2013.01); *C12M 23/34* (2013.01); *C12M 27/22* (2013.01); *C12M 29/00* (2013.01)

(58) Field of Classification Search
CPC ...... C12M 23/16; C12M 29/00; C12M 35/04; C12M 25/14; C12M 21/08; C12M 23/34; C12M 27/22
See application file for complete search history.

(56) References Cited

U.S. PATENT DOCUMENTS 8,496,884 B2 *  7/2013  Murakami ............... B01F 31/87
                                                    422/549
9,034,640 B2 *  5/2015  Matos .................... C12M 25/14
                                                    435/297.1
(Continued)

FOREIGN PATENT DOCUMENTS

EP        3029135 A1     6/2016
WO     2014090993 A1     6/2014
(Continued)

*Primary Examiner* — Shogo Sasaki
(74) *Attorney, Agent, or Firm* — Hudak, Shunk & Farine Co. LPA

(57) ABSTRACT

A fluidic device, a fluidic system and a method for developing a cellular starting material into a three-dimensional cellular structure. The fluidic device includes a base body which includes a chamber in which a matrix is received, into which the cellular starting material to be developed can be introduced, and at least two fluid reservoirs. Each fluid reservoir includes a fluid inlet, a fluid outlet and a separating device which is partially permeable to a fluid medium and which separates the associated fluid reservoir from the chamber and forms a common plane interface with the chamber, via which the fluid medium can diffuse into the matrix. When using suitable fluid media, the fluidic device is adapted to form at least one concentration gradient, at least two mutually orthogonal concentration gradients and/

(Continued)

or at least two mutually antiparallel concentration gradients in the matrix, each of which are essentially homogeneous or deliberately inhomogeneous in the z-direction over at least a section of the extension of the matrix.

20 Claims, 4 Drawing Sheets

(56) References Cited

U.S. PATENT DOCUMENTS

| | | | |
|---|---|---|---|
| 12,031,115 B2 * | 7/2024 | Ranga | C12M 23/20 |
| 2007/0042490 A1 | 2/2007 | Welter et al. | |
| 2008/0141784 A1 * | 6/2008 | Murakami | B01F 31/87 |
| | | | 73/861.18 |
| 2008/0261298 A1 | 10/2008 | Yonekawa | |
| 2011/0226686 A1 * | 9/2011 | Maurer | B01D 69/02 |
| | | | 210/206 |
| 2015/0298123 A1 | 10/2015 | Block, III et al. | |
| 2017/0240854 A1 | 8/2017 | Machluf et al. | |
| 2018/0030409 A1 | 2/2018 | Lewis et al. | |
| 2021/0054322 A1 * | 2/2021 | Ranga | C12M 29/04 |
| 2023/0062382 A1 * | 3/2023 | Atzler | C12M 23/44 |

FOREIGN PATENT DOCUMENTS

| | | |
|---|---|---|
| WO | 2017059171 A1 | 4/2017 |
| WO | 2017083705 A1 | 5/2017 |
| WO | 2017123791 A1 | 7/2017 |

* cited by examiner ced sufficiently large. In the sense of the present invention, this means in particular that the three-dimensional cellular structures have reached a degree of differentiation, size and/or organization that comes close to that of the natural organ in a way that when used in the disease model particular meaningful results can be achieved. Achieving the same differentiation, size and/or organization that a natural organ exhibits is naturally extremely difficult. As a rule, however, this is not necessary. From a certain degree of differentiation, size and/or organization, very meaningful results can be achieved, in particular results that exceed the results that can be achieved in the prior art. Previous organoids from the prior art are not sufficiently well differentiated, large and/or organized. In the case of brain tissue, for example, this means that individual areas develop only randomly, not sufficiently differentiated, imprecisely and/or incorrectly arranged in the forebrain, midbrain and hindbrain.

FLUIDIC DEVICE, FLUIDIC SYSTEM, AND METHOD FOR DEVELOPING THREE-DIMENSIONAL CELLULAR CONSTRUCTIONS

FIELD OF THE INVENTION

The present invention relates to a fluidic device, a fluidic system and a method for developing a cellular starting material into one or more three-dimensional cellular structure(s), while applying at least one concentration gradient to the cellular starting material.

BACKGROUND OF THE INVENTION

The lack of availability of vital patient tissue is currently an obstacle in medical research. This applies in particular to tissues of the central nervous system, such as brain tissue. For this reason, different types of stem or progenitor cells (for example induced pluripotent stem cells (iPS cells), i.e. cells taken from tissue and reprogrammed into stem cells, embryonic stem cells (ES cells), organ-specific stem cells) are used for cell culture growing as a disease model. However, such cell cultures have so far mainly been grown as 2D cultures. 3D cultures (for example organoids), which have the potential to deliver more meaningful results, have so far not been able to be produced, or can only be produced in insufficient quality and with too small dimensions. This also applies to three-dimensional structures based on other cell or tissue types, for example accessible diseased patient tissue such as tumor tissue. Above all, a spatially correct arrangement of cell types (along tissue, organ and body axes), a sufficient differentiation and a sufficient size of the cellular structures in the millimeter to centimeter range cannot be achieved with the currently available methods and devices.

Documents US 2018/0030409 A1, WO 2017/083705 A1 and WO 2014/090993 A1 disclose, for example, methods for developing three-dimensional organoids in which the supply of cell cultures with nutrient media is realized by means of a rotating bioreactor. Here the position of the organoid or the cells contained in the organoid is not fixed relative to the ingredients of the nutrient medium. The use of such rotating bioreactors has the disadvantage that individual tissue or organ areas develop randomly arranged and in an uncontrolled manner, which leads to an inadequate quality of the developed organoids for research purposes.

Furthermore, document WO 2017/123791 A1 describes a static in vitro development of three-dimensional organoids, wherein the cells likewise develop arranged at random and in an uncontrolled manner.

Furthermore, from document US 2015/0298123 A1, a platform with microfluidic systems for cultivating organoids is known. However, the duration of the cultivation and thus the quantitative development of the organoids is limited due to the small dimensions of the microfluidic systems, i.e. the organoids no longer have enough space for further development from a certain size.

It is therefore an object of the present invention to overcome the disadvantages of the prior art. In particular, it is an object of the invention to provide a device, a system and a method by means of which a cellular starting material (one or more cell(s), cell group(s) or tissue) can be developed into a three dimensional cellular structure (organ, organoid, tissue, or cell group) and/or kept in a reproducible manner, so that this structure is sufficiently spatially organized, sufficiently differentiated and dimensioned suffi- The objects are achieved by a fluidic device, a fluidic system and a method according to the independent claims. Developments and embodiments of the fluidic device, the fluidic system and the method are subject matter of the dependent claims and the description below.

SUMMARY OF THE INVENTION

The fluidic device according to the invention for developing a cellular starting material (one or more cell(s), cell group(s), tissue) into one or more three-dimensional cellular structures and for further development, improved maturation, promotion of size growth and/or maintenance of three-dimensional cellular structures comprises a base body with a chamber extending in an x-direction, a y-direction orthogonal to the x-direction and a z-direction orthogonal to the x-direction and the y-direction, in which a matrix (for example comprising a hydrogel) is received or can be received, for example in such a way that the matrix essentially completely fills the chamber. The matrix serves, among others, as a framework to ensure a defined position and alignment of the structures within the chamber. At the same time, it can influence the growth, maturation and maintenance of the structures. Maintenance means in particular the prevention of cell death through permanent supply of medium. The chamber and thus the matrix that is received or can be received therein can preferably extend in each of the three directions (x, y, z) by several hundred micrometers, more preferably at least one millimeter, further preferably several millimeters, further preferably at least 3 mm, further preferably at least 4 mm, further preferably at least 6 mm, even more preferably at least 9 mm, even more preferably several centimeters, even more preferably at least 5 cm, even more preferably at least 7 cm, even more preferably at least 10 cm, wherein the amount of extension in the three directions can be the same or different.

The base body of the fluidic device according to the invention further comprises at least two fluid reservoirs, which are preferably fluidically separated from one another. Fluidically separated from one another means in particular that the fluid reservoirs are each designed as separate cavities and no direct fluid exchange between the fluid reservoirs occurs. In this case, at most, an indirect fluid exchange would merely be possible via the chamber or the matrix. In particular, the base body can comprise at least four fluid reservoirs.

Each of the at least two fluid reservoirs comprise a fluid inlet for preferably continuously introducing a fluid medium into the associated fluid reservoir, a fluid outlet for preferably continuously discharging the fluid medium from the associated fluid reservoir, and a separating device partially permeable to the fluid medium. The separating device separates the respective associated fluid reservoir from the chamber and forms a common plane interface between the associated fluid reservoir and the chamber, via which the fluid medium can diffuse into the matrix. In other words, the base body thus comprises at least four separate fluid inlets, at least four separate fluid outlets and at least four separate separating devices. Since each of the at least four fluid reservoirs has its own fluid inlet, different fluid media can flow through the fluid reservoirs according to the invention.

The fluidic device according to the invention is adapted, when using suitable fluid media, to form at least one concentration gradient, at least two mutually orthogonal and/or at least two mutually antiparallel concentration gradients in the matrix, each of which is essentially homogeneous or deliberately inhomogeneous over at least a section of the extension of the matrix in the z-direction. The at least one concentration gradient, the at least two mutually orthogonal and/or the at least two mutually antiparallel concentration gradients in the matrix are preferably substantially homogeneous over almost the entire extension of the matrix in the z-direction.

The concentration gradient or the concentration gradients can in particular be gradients of the concentration of substances (for example of morphogens or of molecules which influence morphogenic signalling paths or differentiation signalling paths). Concentration gradients in the sense of the present invention can be continuous or discontinuous. Thus, in certain embodiments, the term concentration gradient can also encompass complicated, non-monotonic concentration profiles. For example, the term concentration gradient can also include unstable concentration gradients with temporarily high concentrations in the matrix, which can be formed by applying pressure to the fluid reservoirs in a pulsed manner. It is therefore to be understood that suitable fluid media are fluid media which in principle allow a concentration gradient to be formed.

The mutually orthogonal and/or antiparallel concentration gradients can be formed by means of the fluidic device according to the invention due to the specific structural design and arrangement of the separating devices with respect to one another and in connection with the chamber and the fluid reservoirs. The fluidic device according to the invention thus enables the formation of defined concentrations of biological or non-biological substances in all dimensions of the matrix. The terms orthogonal and antiparallel relate to the direction vectors of the concentration gradients. The term antiparallel thus denotes concentration gradients which have opposite directions with respect to one another.

This specific design and arrangement provides that two of the plane separating devices each extend in the z-direction and the x-direction, wherein these two separating devices being arranged opposite to one another and being spaced apart from one another by the chamber in the y-direction. In this way, when using different fluid media in the fluid reservoirs of the two separating devices spaced apart in the y-direction, a concentration gradient extending in the y-direction between these two separating devices or two concentration gradients extending antiparallel to one another in the y-direction between these two separating devices can be formed. The two of the separating devices can preferably extend in the z-direction and the x-direction over several hundred micrometers, more preferably at least one millimeter, more preferably several millimeters, more preferably at least 3 mm, more preferably at least 4 mm, more preferably at least 6 mm, even more preferably at least 9 mm, even more preferably several centimeters, even more preferably at least 5 cm, even more preferably at least 7 cm, even more preferably at least 10 cm, wherein the amount of extension can be the same or different in the two directions. The two of the separating devices can preferably be spaced apart from one another in the y-direction by several hundred micrometers, further preferably at least one millimeter, further preferably several millimeters, further preferably at least 3 mm, further preferably at least 4 mm, further preferably at least 6 mm, even more preferably at least 9 mm, even more preferably several centimeters, even more preferably at least 5 cm, even more preferably at least 7 cm, even more preferably at least 10 cm.

Furthermore, this specific design and arrangement provides that additional or alternatively two further separating devices each extend in the z-direction and the y-direction, wherein these two further separating devices being arranged opposite to one another and being spaced apart from one another by the chamber in the x-direction. As a result, when using different fluid media in the fluid reservoirs of the two separating devices spaced apart in the x-direction, a concentration gradient extending in the x-direction between these two separating devices or two mutually antiparallel concentration gradients extending in the x-direction between these two separating devices can be formed. The two further separating devices can preferably extend in the z-direction and the y-direction over several hundred micrometers, more preferably at least one millimeter, more preferably several millimeters, more preferably at least 3 mm, more preferably at least 4 mm, more preferably at least 6 mm, even more preferably at least 9 mm, even more preferably several centimeters, even more preferably at least 5 cm, even more preferably at least 7 cm, even more preferably at least 10 cm, wherein the amount of extension can be the same or different in both directions. The two further of the separating devices can preferably be spaced apart from one another in the x-direction by several hundred micrometers, more preferably at least one millimeter, further preferably several millimeters, further preferably at least 3 mm, further preferably at least 4 mm, further preferably at least 6 mm, even more preferably at least 9 mm, even more preferably several centimeters, even more preferably at least 5 cm, even more preferably at least 7 cm, even more preferably at least 10 cm.

A plane interface is accordingly preferably an interface extending in the z direction and in at least one further spatial direction orthogonal thereto (the x-direction or the y-direction).

Each of the separating devices can preferably extend exclusively in the directions described above, that is to say, for example, only in the z-direction and the x-direction or only in the z-direction and the y-direction. In other words, they can span a z-x-plane or a z-y-plane. If separating devices are designed with the same dimensions, which extend exclusively in the directions described above (i.e. only in the z-direction and the x-direction or only in the z-direction and the y-direction), the arrangement and design of the two further of the separating devices described above, in other words represents an arrangement and design of the two of the separating devices rotated by 90 degrees about an axis extending in the z-direction.

In particular, the one of the fluid reservoirs of opposing separation devices can be flown through by a fluid medium in the form of a cell culture medium with one or more additional biological or non-biological substances (for example, morphogens, morphogenic signalling path or differentiation signalling paths influencing molecules, nutrients, growth factors, drugs), while the other fluid reservoir is flown through by a fluid medium in the form of either a cell culture medium without these additional substances (to form a concentration gradient extending between them) or a cell culture medium with other substances (to form two antiparallel concentration gradients extending between them). Thus, due to the structural arrangement and design of the components of the fluidic device at one side of the matrix, a cell culture medium with a substance (e.g. morphogen) can diffuse into the matrix via one of the partition walls and on an opposite side of the matrix a cell culture medium without or with another substance (e.g. morphogen) can diffuse into the matrix via another one of the partition walls, so that a concentration gradient or two antiparallel concentration gradients develop over time between opposite sides of the matrix. When using fluid media with drugs, the device according to the invention can be used for drug tests with three-dimensional cellular structures in order to measure the concentration dependence of cell effects.

Since the chamber or the matrix received or to be received therein has several pairs (at least two pairs) of mutually opposite sides which are adjacent to one another, by means of the fluidic device according to the invention in addition or as an alternative to the antiparallel concentration gradients mutually orthogonal concentration gradients can be formed in the matrix. The two cell culture media with substances can differ from one another.

It goes without saying that, depending on the application or the fluid media used, with the fluidic device according to the invention, optionally at least one concentration gradient, at least two concentration gradients (two orthogonal concentration gradients or two antiparallel concentration gradients), at least three concentration gradients (two mutually antiparallel concentration gradients and one concentration gradient orthogonal thereto) or at least four concentration gradients (two mutually antiparallel concentration gradients and two mutually antiparallel concentration gradients orthogonal thereto) can be formed. In principle, due to its structural configuration, the fluidic de-vice according to the invention can be suitable for forming at least two concentration gradients in the matrix. It goes without saying that the fluidic device only needs to comprise two fluid reservoirs with associated (i.e. two opposing) separating devices for forming only one concentration gradient or two mutually antiparallel concentration gradients. It is also understood that the fluidic device must include four fluid reservoirs with associated (i.e. two pairs of mutually opposite) separating devices in order to form two mutually orthogonal, three or four concentration gradients.

A homogeneity of the concentration gradient(s) over at least a section of the extension, preferably over the entire extension, of the matrix in the z-direction is achieved through the structural formation of the fluid reservoirs in connection with the components of the fluidic device structurally or functionally associated thereto, such as in particular the associated separating devices, the chamber and the fluid inlets and fluid outlets. By means of the respective associated fluid inlets and fluid outlets, the fluid reservoirs can be flown through continuously and thus be continuously supplied with fresh fluid media. Thus, a continuous exchange of fresh and old fluid medium can be provided in order to achieve an optimal supply of nutrients and to remove waste materials. At the same time, the fluid reservoirs ensure that the inflowing fluid medium accumulates in the fluid reservoir to a predetermined extent, so that the entire partially permeable separating device is always completely covered with fluid medium on a side facing the associated fluid reservoir, i.e. over the entire surface of the separating device. As a result, the volume and the concentration of the fluid medium diffusing into the matrix via each of the separating devices can be kept constant over the entire z-extension of the respective separating device, as a result of which a homogeneous concentration gradient forms in the matrix at least over a section of the extension, preferably over the entire extension of the matrix in the z-direction.

A homogeneous concentration gradient in the z-direction preferably means that the ratio of the concentration of substances (e.g. morphogens) at a first position z1 and at a second position z2 is in a range from 0.8:1 to 1.2:1, further preferably from 0.9:1 to 11:1, more preferably from 0.95:1 to 1.05:1, wherein the position z1 is different from position z2 only in relation to the z-direction, but not in relation to the x-direction and the y-direction. In particular, the stated ratios of the substance concentrations apply preferably to all such positions $z_n$ and $z_m$ over the entire z extension. In other words, a homogeneous concentration gradient in the z-direction preferably means that the gradient does not differ or only differs insignificantly, in particular within the scope of the above ratios of substance concentrations, in different planes spanned by the x-direction and the y-direction along the z-extension.

In contrast, an inhomogeneous concentration gradient preferably means that the ratio of the concentration of substances (e.g. morphogens) at a first position $z_1$ and at a second position $z_2$ is less than 0.8:1 or greater than 1.2:1, wherein position $z_1$ differs from position $z_2$ only with respect to the z-direction, but not with respect to the x-direction and the y-direction. In particular, the stated ratios of the substance concentrations apply preferably to all such positions $z_n$ and $z_m$ over the entire z-extension. In other words, an inhomogeneous concentration gradient in the z-direction preferably means that the gradient differs in different planes spanned by the x-direction and the y-direction along the z-extension within the scope of the above-mentioned ratios of the substance concentrations.

A predetermined (deliberately) inhomogeneity of the concentration gradient(s) can be achieved, for example, in that one or each of the separating devices has different partial permeabilities within the separating device. For example, a higher concentration difference between two opposite sides can be set in the center of the chamber than in the lateral areas of the chamber. A deliberate inhomogeneity differs from a indeliberate (random) inhomogeneity in that the former can be set in a defined and reproducible manner by use of appropriate measures. In further embodiments, in addition to the above-described homogeneity or deliberate inhomogeneity of the con-centration gradient in the z-direction, an additional homogeneity or an additional deliberate inhomogeneity in a spatial direction can be set that is orthogonal both to the z-direction and the direction of the concentration gradient. The above statements on the homogeneity and the deliberate inhomogeneity of the concentration gradient in the z-direction apply accordingly to this additional homogeneity or additional deliberate inhomogeneity over the stated spatial direction.

By forming at least two mutually orthogonal and/or antiparallel concentration gradients in the matrix containing the cellular starting material, which each are homogeneous or deliberately inhomogeneous over an extension of the matrix in the z-direction, the three-dimensional development of the cellular starting material into the three-dimensional cellular structure (e.g. a cell culture to an organoid) can be controlled spatially. The fluidic device according to the invention thus enables the deliberate simultaneous development of several tissue areas, e.g. dorsal and ventral forebrain, midbrain and hindbrain. It goes without saying that in addition to brain tissue, other organ tissue can also be developed by means of the fluidic device according to the invention. In addition, the use of the fluidic device according to the invention increases the reproducibility of developed organoids compared to known systems, since the concentration gradients can be deliberately formed in the matrix in terms of space and intensity by means of the fluidic device.

In addition, by the extension of the chamber and the matrix which is received therein or can be received therein in three different spatial directions, a three-dimensional cellular structure can be developed in larger dimensions than has been possible with previous devices. Thus, with certain embodiments of the fluidic device according to the invention, the development of cellular structures in the millimeter range up to the centimeter range can be realized.

Compared to devices of the prior art, the fluidic device according to the invention has the further advantage that the pressure in the individual fluid reservoirs and thus on different sides of the matrix can be regulated via a controlled introduction and discharge of fluid media into and out of the fluid reservoirs. In this way, fresh nutrients can be supplied into the interior of comparatively large cellular structures in a targeted manner by means of pressurization and/or the drainage of metabolic waste products can be promoted by means of pressure reduction. These effects can be very important for a growth in size and/or the maintenance of large organoids and other cellular structures and open up additional applications for the fluidic device. This cannot be achieved by means of known devices of the prior art, which is why, above a certain organoid size (typically in the small mm range), cells inside the organoid are only poorly supplied and die because the diffusion path of ingredients of the nutrient medium into the inside of the organoid becomes too large and the transport of nutrient medium ingredients, moreover, cannot be improved by increasing the pressure in the nutrient medium surrounding the organoid. The achievable growth in size is also limited due to the lack of supply by means of known devices.

One embodiment relates to a fluidic device comprising a base body which comprises a chamber extending in an x-direction, a y-direction orthogonal to the x-direction and a z-direction orthogonal to the x-direction and the y-direction, in which a matrix is received or can be received, into which the starting material to be developed can be introduced; and at least four fluid reservoirs. Each of the at least four fluid reservoirs comprises a fluid inlet for introducing a fluid medium into the associated fluid reservoir, a fluid outlet for discharging the fluid medium from the associated fluid reservoir, and a separating device which is partially permeable to the fluid medium and which separates the associated fluid reservoir from the chamber and forms a common plane interface of the associated fluid reservoir with the chamber, via which the fluid medium can diffuse into the matrix. When using suitable fluid media, the fluidic device is designed to form at least two mutually orthogonal and/or antiparallel concentration gradients in the matrix, each of which is essentially homogeneous over at least a section of the extension of the matrix in the z-direction, in that two of the separating devices each extend in the z-direction and the x-direction and are arranged opposite to one another and are spaced apart from one another by the chamber in the y-direction, and in that two more of the separating devices each extend in the z-direction and the y-direction and are arranged opposite to one another and are spaced from one another by the chamber in the x-direction.

In one embodiment of the fluidic device, the chamber can have a rectangular, preferably a square, cross section. Accordingly, the matrix which is received or can be received therein can also have a corresponding rectangular, preferably square, cross section.

In a further development, the separating devices of the fluidic device can be connected to one another and together form the chamber disposed between them. More specifically, adjacent separating devices may have a common edge extending in the z-direction. In this development, the intermediate chamber can be delimited by the separating devices and thus be defined in terms of its shape and extension. In this case, mutually opposing separating devices can be spaced apart from one another by separating devices disposed between them with a different orientation in the x-direction or in the y-direction.

According to one embodiment of the fluidic device, each of the separating devices can be formed in the form of a partition wall provided with a plurality of through openings. The through openings can be distributed uniformly and/or according to a specific pattern over the entire partition wall. By means of unevenly distributed and/or unevenly large openings in a partition wall an inhomogeneous concentration gradient can be deliberately produced, which, for example, is different over the extension of the matrix in the z-direction and thus influences different areas of the structure differently along the z-direction. Correspondingly, an inhomogeneous concentration gradient, i.e. a different concentration difference, can be deliberately formed over the extension of the matrix in the x-direction and/or in the y-direction. In particular, to this end the number of through openings can be varied in the corresponding direction. Forming one or more inhomogeneous concentration gradients makes it possible to produce different effects at different positions in a three-dimensional cellular structure.

The partition walls can each be provided with 0.5 to 50, preferably 0.5 to 5, preferably 1.5 to 4, more preferably 2 to 3.5, even more preferably 2.5 to 3 through openings per mm2. The through openings can in particular have a circular cross section with a diameter between 0.1 mm and 1.5 mm, preferably 0.2 mm and 1.2 mm, more preferably between 0.4 mm and 1.0 mm, further preferably between 0.5 mm and 0.8 mm. The through openings within a partition wall and between the different partition walls can have the same cross-sectional area or different cross-sectional areas. The partition walls can also each have the same number or different numbers of through openings. Side walls perforated in this way serve to keep the system stable and to allow fluid medium to pass through in a predetermined amount. The thickness of the partition walls is chosen so that the mechanical stability of the fluidic device is guaranteed. At the same time, partition walls that are as thin as possible are desired so that the fluid media with substances can diffuse as unhindered as possible through the perforated walls. For this purpose, the partition walls can have a thickness between 0.05 mm and 1.5 mm, preferably between 0.1 mm and 1 mm. The thickness of the partition walls as well as the number, size, geometry and arrangement of the through openings can be selected so that the partition devices are partially permeable to the fluid media used, but at the same time the matrix is prevented from passing through the through openings.

As an alternative to separating devices in the form of partition walls, in other embodiments separating devices in the form of membranes, grid arrangements or the like can be formed.

In a further development of the fluidic device, the chamber can comprise an inlet opening and an outlet opening, between which the chamber extends in the z-direction. The inlet opening and the outlet opening are congruent to one another as viewed in the z-direction, or at least overlap, so that the chamber can be transilluminated in the z-direction by means of optical beams. In this way, for example, a continuous analysis of the differentiating organoids is enabled during development, since the chamber is continuous in the middle and opened upwards and downwards via the inlet opening and the outlet opening. In particular, the further development of the chamber with the inlet opening and the outlet opening enables the use of a microscope to observe and analyze the cellular starting material or the three-dimensional cellular structure (e.g. the cell culture or the organoid) during development. In addition, the further development with an inlet opening and an outlet opening represents an open system in which the matrix in the chamber can exchange gas with ambient air.

The further development described above makes the fluidic device microscopable, but restricts the number of orthogonal and/or antiparallel concentration gradients that can be formed in the matrix to a maximum of four different concentration gradients (two mutually antiparallel x-concentration gradients that extend along the x-direction, as well as two y-concentration gradients which are orthogonal thereto and mutually antiparallel and which extend along the y-direction). However, this is sufficient for almost all practice-relevant applications, since most tissues/organs develop along two main axes (anterior-posterior [front-back] and dorsal-ventral [top-bottom]). However, in an alternative further development of the fluidic device, the formation of a total of six concentration gradients in the matrix can be made possible (two x-concentration gradients which are mutually antiparallel and extend along the x-direction, two y-concentration gradients which are orthogonal thereto and mutually antiparallel and extend along the y-direction, as well as two z-concentration gradients which are orthogonal thereto and mutually antiparallel and extend along the z-direction). In this case, the development can be controlled along the anterior-posterior axis, the dorsal-ventral axis, and the right-left axis. In such an alternative development, the fluidic device, more precisely the base body, comprises two additional of the separating devices, which each extend in the x-direction and the y-direction, wherein these two additional separating devices are arranged opposite to one another and are spaced from each other by the chamber in the z-direction. In this way, when using different fluid media in the fluid reservoirs belonging to these two separating devices spaced apart in the z-direction, a third concentration gradient lying between these two separating devices can be formed.

In one embodiment, the fluidic device can furthermore comprise a cover which is or can be connected to the base body and which seals at least one or all of the at least four fluid reservoirs towards one side in the z-direction. The cover can in particular be releasably connected or connectable to the base body, for example by means of a screw connection. The cover can also extend in sections over the inlet opening of the chamber and close it at least partially in the z-direction, wherein the cover can comprise a cover recess which is aligned with the inlet opening of the chamber in the z-direction. Thus, during the development of the three-dimensional cellular structure, the course of development can be observed through the cover recess, in particular examined under a microscope. By selecting the area of the cover recess to be smaller than the area of the inlet opening of the chamber, the cover can also serve to prevent undesired leakage of the matrix in the z-direction.

The fluidic device can further comprise a bottom component which is or can be connected to the base body and which sealingly closes at least one or all of the at least four fluid reservoirs towards another side in the z-direction, wherein the bottom component is arranged on a side of the chamber opposite the cover. The bottom component can be releasably connected or connectable to the base body, for example by means of a screw connection. In addition, the bottom component can extend in sections over the outlet opening of the chamber and can at least partially close it in the z-direction, wherein the bottom component can comprise a bottom recess which is aligned with the outlet opening of the chamber in the z-direction. Thus, during the development of the organoid, the course of development can be observed through the bottom recess or the cover recess and the bottom recess, in particular examined under a microscope. Thus, moreover, a simple insertion and removal of structures into/from the chamber is possible. By selecting the area of the bottom recess to be smaller than the area of the outlet opening of the chamber, the bottom component can also serve to prevent undesired leakage of the matrix in the z-direction. The capability of the fluidic device for microscopically examination can be further improved in that the bottom component is preferably provided with a cover glass in the area of the bottom recess.

At least one of the fluid reservoirs can be designed to be open in order to enable a connection to an incubator.

The bottom component can be designed in the form of a truncated cone or a truncated pyramid, the top surface of which adjoins the base body. As a result, the bottom component can serve as the foot of the fluidic device and support the base body in a stable manner with respect to a subsurface.

In one embodiment, the bottom component can be provided with recesses, grooves, channels or the like. These can be arranged at the base component and designed in such a way that, when the base body and the bottom component are connected to one another, a respective one of the recesses, grooves, channels or the like is adjacent to a respective one of the fluid outlets of the fluid reservoirs, in order to discharge the fluid media continuously exiting the fluid outlets in a targeted manner, for example into one or more adjacent collecting containers.

The base body of the fluidic device can be made of metal, preferably of stainless steel, glass, ceramic or polymer. The other components of the fluidic device can also be made from one of these materials, preferably from the same material as the base body. In particular, the components of the fluidic device can be made from a material that is autoclavable, non-cell-toxic and non-autofluorescent. The fact that the material used can be autoclaved enables the fluidic device to be reused. In addition, cell-toxic materials are to be avoided, as they do not hinder the growth of the cellular starting material to be developed. The use of non-autofluorescent materials ensures that no undesired interferences occur when examining fluorescent components under the microscope.

The matrix serves to hold the cellular starting material to be developed or the developing three-dimensional cellular structure in the intended position during development, preferably in the center of the chamber. Moreover, multiple three-dimensional cellular structures can be received in a single chamber. In addition, the matrix allows the quantitative growth and differentiation of the cellular starting material. Moreover, the matrix allows the diffusion of fluid media. Optically transparent material is preferably used as the matrix in order to enable observation of the development of the starting material or the development of three-dimensional cellular structures over time. The matrix can in particular be a hydrogel matrix. The matrix can in particular be an agarose matrix. Alternatively, a collagen matrix, a basement membrane-like matrix (for example Matrigel®), a synthetic matrix or the like can be used as the matrix. A matrix made of agarose has the advantage that it consists of defined components, the composition of which does not fluctuate. An agarose matrix allows reproducible conditions and does not negatively affect the differentiation and the growth in size. The concentration and thus the diffusion properties of an agarose matrix can be changed. An agarose matrix is cheaper than Matrigel® and its composition can easily be standardized.

The agarose content in the matrix is preferably in a range from 0.4-1.2% by weight. A very high proportion of agarose is disadvantageous, since otherwise the growth in size of the organoid can be hindered. However, the agarose content should not be very small either, since otherwise the stability and pressure resistance of the matrix can be reduced and the matrix can fall out of the interior of the chamber. In addition, the agarose content should be sufficiently high in order to keep the position of the three-dimensional cellular structure stable. A combination of different agarose concentrations in the inner area of the chamber and at the outer area (towards the partition walls) is possible. In general, combinations of different matrix substances are possible. In some embodiments, the matrix comprises various substances.

In a further development of the fluidic device according to the invention, the fluid inlet and the fluid outlet of each fluid reservoir can be spaced apart from one another in the z-direction and preferably arranged on a line extending in the z-direction. In other words, the fluid inlet and the fluid outlet of each fluid reservoir can have a vertical arrangement. This enables an optimal continuous flow through each fluid reservoir. The flow through the fluid reservoirs can be further improved in that, in certain embodiments, the fluid outlet of each fluid reservoir has a larger cross-sectional area than the fluid inlet of the same fluid reservoir. Alternatively, the fluid inlet and the fluid outlet of each fluid reservoir can have a horizontal or other arrangement. The fluid inlet and the fluid outlet of each fluid reservoir can, for example, be arranged at a 24 degree angle to one another. The fluid inlets and fluid outlets can each have a smaller diameter towards the reservoir. When tubing is connected to the fluid inlets and/or fluid outlets, this can prevent a front end of the tubing from unintentionally entering the reservoir.

The invention also relates to a fluidic system for developing a cellular starting material into one or more three-dimensional cellular structures and for further developing, improving maturation, promoting growth in size and/or maintaining three-dimensional cellular structures. The fluidic system according to the invention comprises a fluidic device of the type described above and a pump system in which each fluid inlet is connected via an inlet hose to a pump for preferably continuously introducing a fluid medium into the associated fluid reservoir. The introduction of fluid medium into each fluid reservoir can thus be controlled in a predetermined manner via the pump system.

Each pump can be adapted to deliver the fluid medium at a flow rate between 1 and 1000 µl/h, preferably between 1 and 100 µl/h, more preferably between 15 and 60 µl/h, further preferably between 20 and 50 µl/h through the fluid inlet. The flow rate is chosen so that per unit of time significantly more fluid medium with substance (e.g. morphogen) is supplied to a fluid reservoir than fluid medium with substance (e.g. morphogen) leaves the fluid reservoir by diffusion, while at the same time a compression of the matrix by the fluid media is avoided. Apart from constant flow rates, the concentration gradients can also be achieved by dynamic flow rates. By setting dynamic flow rates, pressure (pulses) can be applied to the fluid reservoirs dynamically, in particular in a pulsed manner, whereby concentration gradients in the form of complicated, non-monotonous concentration profiles can be formed in the matrix.

Furthermore, defined pressure differences between opposing fluid reservoirs can be produced by means of the pump system. This can be relevant for certain applications, in particular for processes after the development of an organized three-dimensional cellular structure, such as the maintenance of three-dimensional cellular structures or a directed removal of metabolic products.

The pump system can in particular be a syringe pump system. The pumps in this case are syringe pumps.

In a further development of the fluidic system, each fluid outlet of the fluidic device can be connected to an outlet hose for discharging the fluid medium from the associated fluid reservoir. Each outlet hose can preferably be connected to an outlet pump for subjecting the fluid outlet to a pre-determined negative pressure. In this way, the flow rate and thus the flow through the fluid reservoirs with fluid medium can be controlled even better. Pumps can only be connected to the inlet hoses, only to the outlet hoses, or to both at the same time.

In a further embodiment of the fluidic system, at least two, preferably a plurality of fluidic devices of the type described above can be provided which are arranged in the form of a parallel circuit and can be supplied with fluid media in parallel by means of the pump system. Moreover, a parallel circuit using vacuum pump systems at the outlets or a parallel circuit using a combination of inlet and outlet pumps can be realized.

The invention further relates to a method for developing cellular starting material into one or more three-dimensional cellular structures and/or for their maturation, growth in size or maintenance, wherein the method comprises the steps:
  providing the cellular starting material to be developed in a matrix which extends in an x-direction, a y-direction orthogonal to the x-direction and a z-direction orthogonal to the x-direction and the y-direction; and
  forming at least one concentration gradient, at least two mutually orthogonal concentration gradients and/or at least two mutually antiparallel concentration gradients in the matrix, wherein each of the concentration gradients extends in the x-direction or the y-direction and is a concentration gradient which is homogeneous or deliberately inhomogeneous in the z-direction. More precisely, each of the concentration gradients is homogeneous or deliberately inhomogeneous over at least a section of the extension or the entire extension of the matrix in the z-direction.

The concentration gradients can, in particular, be gradients of the concentration of morphogenes, or substances or drugs that influence morphogenic signalling paths or differentiation paths. In some embodiments, the concentration gradients can in particular be gradients of the concentration of morphogens or substances that influence morphogenic signalling paths or differentiation paths. In some embodiments, the concentration gradients can in particular be gradients of the concentration of drugs.

In a further development, the invention also relates to a method for developing cellular starting material into one or more three-dimensional cellular structures and/or for their maturation, growth in size or maintenance, wherein the method comprises the steps:

provides the starting material to be developed (one or more cell(s), cell group(s), or tissue) in a matrix which is received in a chamber of a fluidic device, wherein the chamber and the matrix extend in an x-direction, a y-direction orthogonal to the x-direction and a z-direction orthogonal to the x-direction and the y-direction, and wherein the fluidic device comprises at least two fluid reservoirs fluidically separated from one another, wherein each of the at least two fluid reservoirs comprises a separating device which is partially permeable to the fluid medium and which separates the associated fluid reservoir from the chamber and forms a common plane interface between the associated fluid reservoir and the chamber, and wherein respectively two of the separating devices are arranged on opposite sides of the matrix;

flowing a respective fluid medium through the at least two fluid reservoirs;

forming at least one concentration gradient, at least two mutually orthogonal concentration gradients and/or at least two mutually antiparallel concentration gradients in the matrix, each of which is essentially homogeneous or deliberately inhomogeneous over at least a section of the extension of the matrix in the z-direction, in that the respective associated fluid medium diffuses over the section of the extension of the matrix in the z-direction into the matrix via the partially permeable separating devices of the at least two fluid reservoirs flown through, wherein different fluid media diffuse into the matrix at respective opposite sides of the matrix.

The method can in particular be carried out by means of a fluidic device or a fluidic system of the type described above.

Another aspect of the invention relates to a three-dimensional cellular structure that can be produced by a method of the type described above.

It goes without saying that the subject matter of the invention is not limited to the embodiments and/or developments described above. In addition, it goes without saying that although some of the embodiments, developments and features have been described above only in relation to the fluidic device or the fluidic system, these embodiments, developments and features can apply accordingly to the method according to the invention. Likewise, embodiments, developments and features that have been described above only in relation to the method can apply accordingly to the fluidic device and/or the fluidic system.

BRIEF DESCRIPTION OF THE FIGURES

Exemplary embodiments of the present invention are explained in more detail below with reference to the accompanying schematic figures. In the figures.

DESCRIPTION OF THE FIGURES

Figure 1:
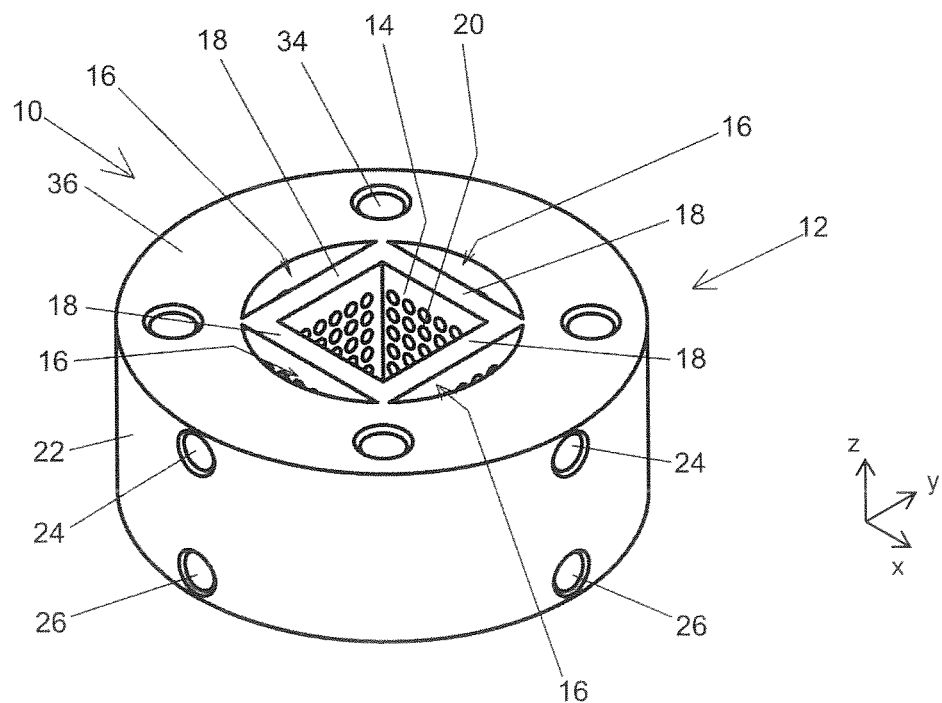
FIG. 1 shows a perspective view of a fluidic device according to an exemplary embodiment.
Figure 2:
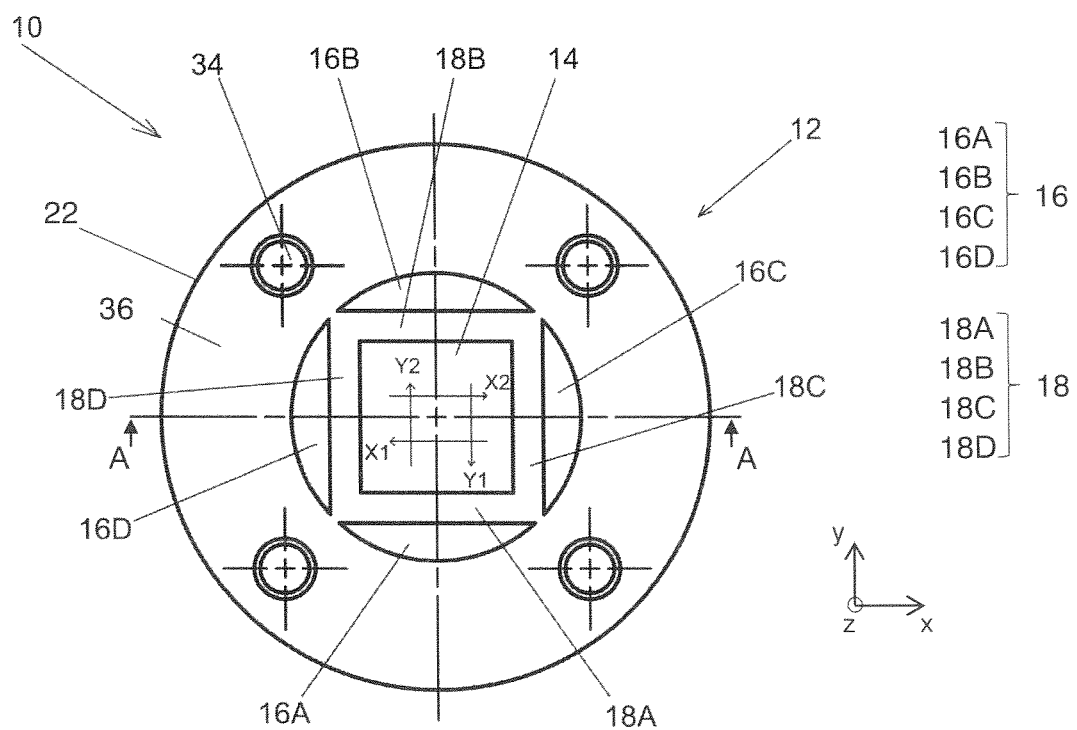
FIG. 2 shows a plan view of the fluidic device according to the exemplary embodiment from FIG. 1.
Figure 3:
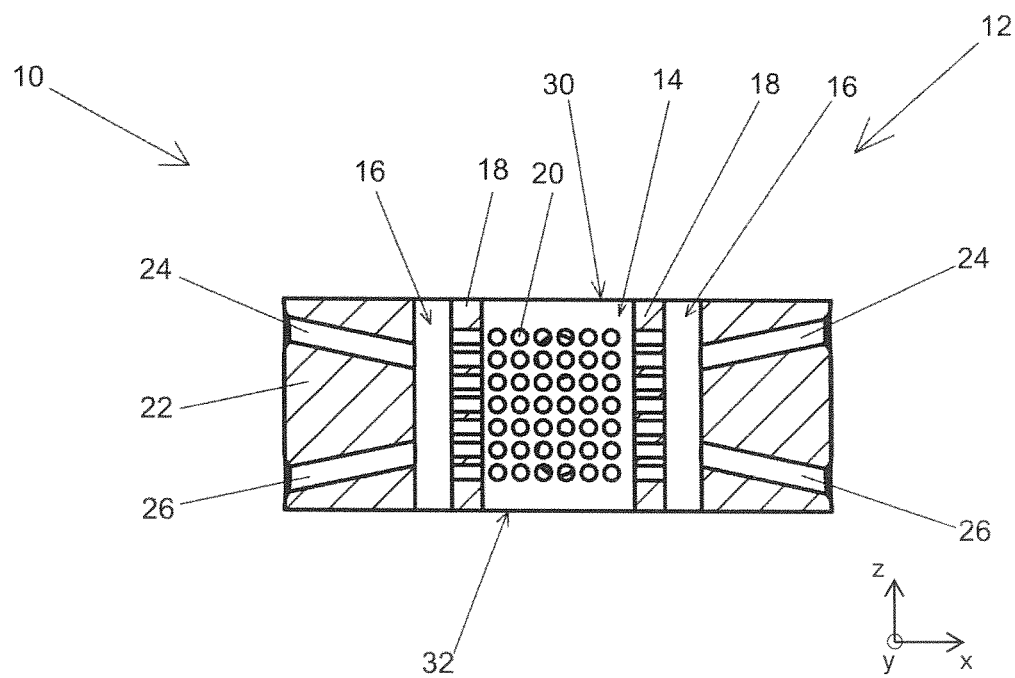
FIG. 3 shows a sectional view of the fluidic device according to the exemplary embodiment from FIGS. 1 and 2.

FIGS. 1 to 3 show an exemplary embodiment of the fluidic device 10 according to the invention in different views, wherein FIG. 1 shows a perspective view, FIG. 2 shows a plan view and FIG. 3 shows a sectional view of the fluidic device 10 along the line A-A in FIG. 2.

The fluidic device 10 comprises a base body 12 in which a chamber 14 is formed which extends in an x-direction, a y-direction orthogonal to the x-direction and a z-direction orthogonal to the x-direction and the y-direction. In the exemplary embodiment shown, the chamber 14 extends several millimeters in each of the three mutually orthogonal directions.

The chamber 14 is intended to receive a matrix (not shown). For example, a hydrogel matrix, in particular an agarose matrix, can be introduced into the chamber 14 and fill it completely. The matrix is used to arrange a cellular starting material introduced into the matrix, which is to be developed into a three-dimensional cellular structure by means of the fluidic device 10, in an intended position within the chamber 14 and to hold it in this position and at the same time to provide an optimal environment for the development, growth in size, maturation and/or preservation.

The base body 12 of the fluidic device 10 further comprises four fluid reservoirs 16, which are separated from one another and completely isolated from one another fluidically. Each of the four fluid reservoirs 16 is separated from the chamber 14 by a separating device 18, wherein the four separating devices 18 are connected to one another and thus form the chamber 14 lying between them. In other words, each of the separating devices 18 delimits an associated fluid reservoir 16 towards one side, while the separating devices 18 jointly delimit the chamber 14 towards their respective other side. Preferably, as in the example shown, the four separating devices 18 form an intermediate chamber 14 which has a square cross-sectional area. In the example shown, the chamber 14 is thus a cuboid with a square cross-section. In the exemplary embodiment shown, the separating devices 18 are each designed in the form of a plane partition wall.

Each of the four separating devices 18 is partially permeable for fluid media that can be introduced into the fluid reservoirs 16. The separating devices 18 thus each represent an interface between an associated one of the four fluid reservoirs 16 and the chamber 14, via which a fluid medium can flow from each of the fluid reservoirs 16 into the chamber 14 and out of the chamber 14. In particular, fluid media can diffuse from the fluid reservoirs 16 via the respective associated separating devices 18 into the matrix received in the chamber 14 and thereby form concentration gradients in the matrix.

In the exemplary embodiment shown in the figures, each of the separating devices 16 is designed in the form of a perforated partition wall with a plurality of through openings 20. For the sake of clarity, a maximum of one of the through openings 20 is provided with a reference symbol in the figures. In the example shown, the through openings each have circular cross-sections with a diameter of approximately 0.5 mm. The number, geometry and size and arrangement of the through openings can be selected depending on the matrix used, depending on the fluid media used, depending on the desired level of the concentration differences and/or depending on the desired homogeneity of the gradients, in order to ensure on the one hand an appropriate contact area between the matrix and the fluid media accumulated in the fluid reservoirs 16 for adjusting the intended diffusion, and on the other hand to prevent the matrix from escaping from the chamber 14 through the through openings 20.

As can be seen in FIGS. 1 to 3, in the exemplary embodiment shown, two of the plane separating devices 18, namely the separating devices 18A and 18B (see FIG. 2), each extend exclusively in the z-direction and the x-direction. These two separating devices 18A, 18B are arranged opposite one another and are spaced apart from one another by the chamber 14 in the y direction. In this way, when using different fluid media in the associated fluid reservoirs 16A, 16B, a concentration gradient (Y1 or Y2) extending in the y-direction between these two separating devices 18A, 18B or two mutually antiparallel concentration gradients (Y1 and Y2) extending in the y-direction between these two separating devices can be formed. Merely for reasons of clarity, the distinction between the fluid reservoirs 16 by the reference symbols 16A to 16D provided for explanation and the distinction of the separating devices 18 by the reference symbols 18A to 18D provided for explanation are only used in FIG. 2.

It can also be seen that in the exemplary embodiment shown, two more of the separating devices 18, namely the separating devices 18C and 18D (see FIG. 2), each extend exclusively in the z-direction and the y-direction, wherein these two further separating devices 18C, 18D are arranged opposite to one another and are spaced apart from one another by the chamber 14 in the x-direction. As a result, when using different fluid media in the associated fluid reservoirs 16C, 16D, a concentration gradient (X1 or X2) extending in the x-direction between these two separating devices 18C, 18D or two mutually antiparallel concentration gradients (X1 and X2) extending in the x-direction between these two separating devices 18C, 18D can be formed.

Thus, with the use of suitable fluid media, up to four concentration gradients can be formed in the matrix by means of the fluidic device 10 shown, namely two pairs of antiparallel concentration gradients (X1, X2 and Y1, Y2), wherein the pairs are orthogonal to one another. It goes without saying that only one, two or three of the concentration gradients X1, X2, Y1, Y2 shown can be formed in certain applications. Due to the extension of the chamber 14 and the separating devices 18, respectively, in the z-direction, all of the concentration gradients X1, X2, Y1, Y2 can be formed homogeneously over the extension of the matrix in the z-direction. This is shown by way of example in FIGS. 7A to 7C and 8A to 8C, which are explained in detail below.

In the exemplary embodiment shown, the base body 12 has an essentially cylindrical shape, wherein the base body 12 comprises a sleeve-shaped shell 22. Each of the four fluid reservoirs 16 is formed in the example by an associated separating device 18 and an associated section or segment of the inner circumferential surface of the sleeve-shaped shell 22. Such a cylindrical configuration of the base body 12 with a sleeve-shaped shell 22 can be advantageous in particular for the manufacture of the fluidic device 10. For example, the sleeve-shaped shell 22 and the separating devices 18 forming the cuboid chamber 14 (with a square cross-section) can be produced separately from one another in a first step. The chamber 14 can then be pressed into the inner recess of the sleeve-shaped shell 22, so that the four longitudinal edges of the cuboid chamber 14 are in contact with the inner circumferential surface of the sleeve-shaped shell 22, more precisely form a press fit therewith. As a result, the four fluid reservoirs 16 are fluidically separated from one another. As an alternative to the production and subsequent the assembly of individual parts, the system can be produced in one step, for example by means of 3D printing.

Each of the fluidic reservoirs 16 is provided with a fluid inlet 24 formed in the base body 12 and a fluid outlet 26 formed in the base body 12 (only two fluid inlets 24 and two fluid outlets 26 can be seen in FIG. 1). The fluid inlets 24 extend from the outside through the shell 22 of the base body 12 to the inside into the fluid reservoirs 16. The fluid outlets 26 extend from an inside of the fluid reservoirs 16 through the shell 22 of the base body 12 to the outside. This can be seen in particular from FIG. 3. The fluid inlets 24 and fluid outlets 26 can be used to continuously flow fluid media through the fluid reservoirs 18. In this way, a continuous exchange of fresh and old fluid medium can be ensured in order to achieve an optimal supply of nutrients. In this way, waste materials that arise in the cells and are present in the reservoirs in low concentrations can also be removed. If an overpressure pump is connected on one side, which generates a higher pressure than at the opposite side, such waste materials are preferably discharged in one direction. The fluidic device can therefore be used as a dynamic system. It goes without saying that the fluid inlets 24 and/or fluid outlets 26 can be fluidically connected to hoses in further exemplary embodiments in order to better supply and/or discharge the fluid media used. The hoses can also be connected to a pump system, for example a syringe pump system, in order to control the flow rate in the individual fluid reservoirs 16. In this way, a flow rate between 20 and 50 µl/h can preferably be set in each of the fluid reservoirs 16. To this end, by means of the pump system, overpressure can be generated at the fluid inlets 24 and/or negative pressure at the fluid outlets 26.

The chamber 14 of the illustrated fluidic device 10 comprises an inlet opening 30 and an outlet opening 32, between which the chamber 14 extends in the z-direction. The inlet opening 30 and the outlet opening 32 are congruent to one another when viewed in the z-direction. As a result, the chamber 14 can be transilluminated by means of optical beams in the z-direction in order to enable the cellular three-dimensional structures, that are produced, to be observed and analyzed by means of a microscope during development. In addition, the fluidic device 10 is designed as an open system by means of the inlet opening 30 and the outlet opening 32 of the chamber 14, wherein the matrix in the chamber 14 can exchange gas with the ambient air.

Furthermore, the base body 12 of the fluidic device 10 in the exemplary embodiment comprises four bores 34 on each of its end faces, wherein only the end face 36 is visible in the figures shown. The base body 12 of the fluidic device 10 can be connected to a cover and/or a bottom component via the bores 34 on the end faces 36.

Figure 4:
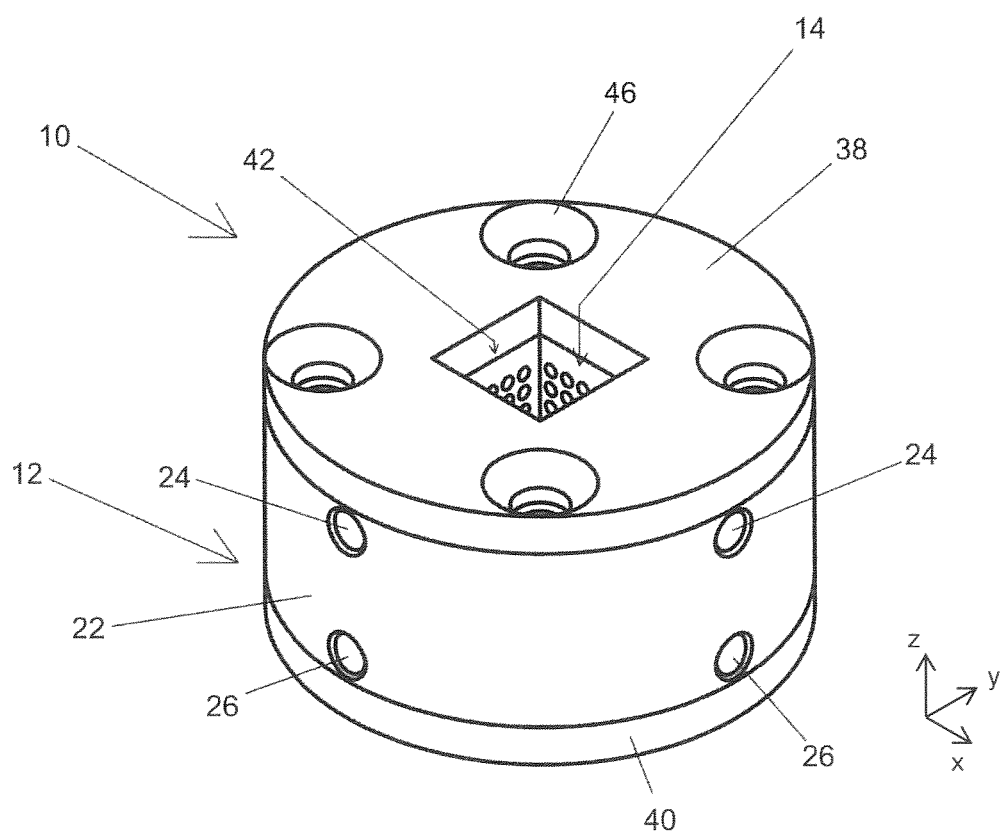
FIG. 4 shows a perspective view of the fluidic device according to the exemplary embodiment from FIG. 1 with a cover and a first bottom component.

FIG. 4 shows a first exemplary embodiment of a cover 38 connected to the base body 12 and a bottom component or bottom plate 40 connected to the base body 12. The cover 38 and the bottom plate 40 are congruent to the end faces of the base body. In addition, the cover 38 and the bottom plate 40 in FIG. 4 are designed to correspond to one another. The cover 38 comprises a cover recess 42 which is aligned in the z-direction with the inlet opening 30 of the chamber 14. Accordingly, the bottom plate 40 is provided with a bottom recess 44 (see FIG. 5) which is aligned with the outlet opening 32 of the chamber 14 in the z-direction. Despite the cover 38 and the bottom plate 40, the fluidic device 10 can thus still represent an open system, with the advantages and effects described above.

For the releasable connection of the cover 38 and the bottom plate 40 to the base body, the cover 38 and the bottom plate 40 likewise have four bores 46. The cover 38 can be connected to the base body 12 by aligning the four bores 46 of the cover 38 with the bores 34 of the base body 12. Then screws or pins can be inserted into the bores. The same applies to the bottom plate 40, although the bores of the bottom component are not shown in the figures.

Figure 5:
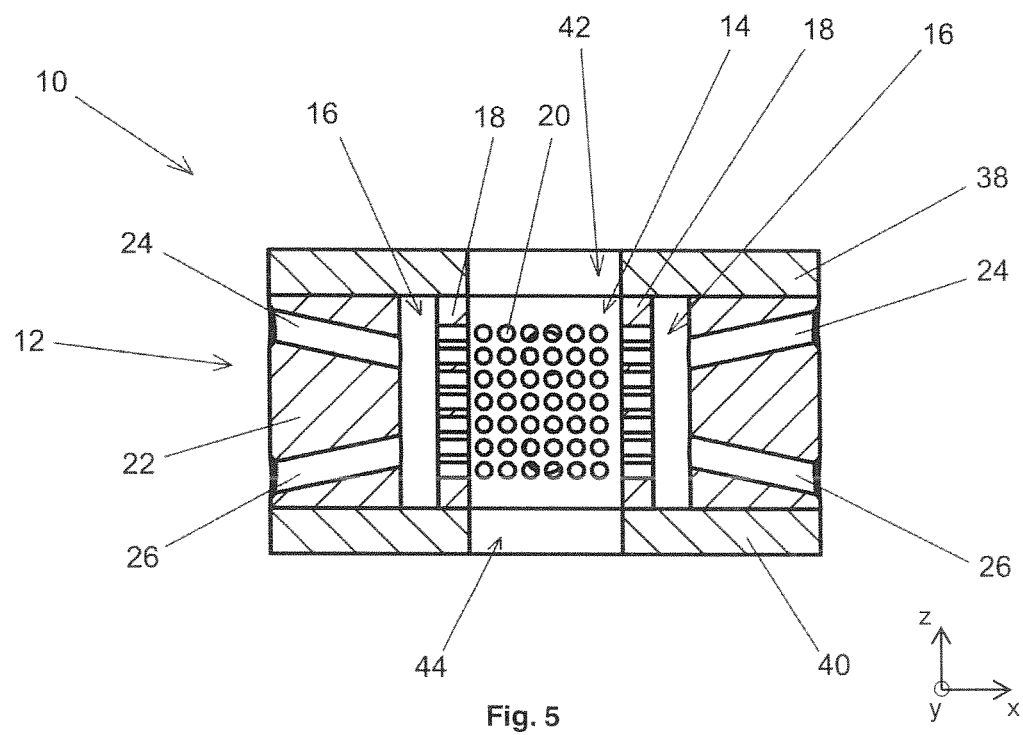
FIG. 5 shows a sectional view of the fluidic device with the cover and the first bottom component according to FIG. 4.

As can be seen in the sectional view in FIG. 5, the cover 38 and the bottom plate 40 close the four fluid reservoirs 16 in the z-direction. More precisely, the cover 38 seals the fluid reservoirs 16 in the z-direction towards one side (upwards in the illustration shown), while the bottom plate 40 seals the fluid reservoirs 16 in the z-direction towards an opposite side (downwards in the illustration shown). Thus, fluid media can only get into the fluid reservoirs 16 or out of the fluid reservoirs 16 via the fluid inlets 24, the fluid outlets 26 and the partially permeable separating devices 18.

Figure 6:
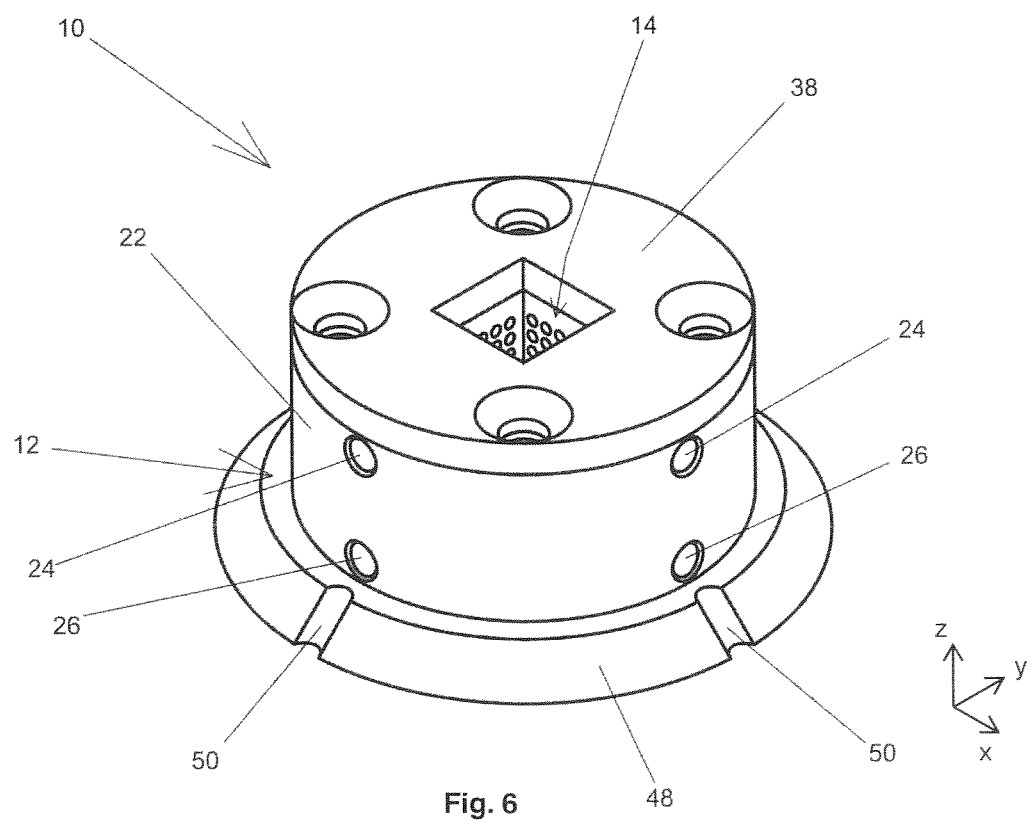
FIG. 6 shows a perspective view of the fluidic device according to the exemplary embodiment from FIG. 1 with a cover and a second bottom component.

FIG. 6 shows a second exemplary embodiment of a cover 38 connected to the base body 12 and a bottom component or bottom plate 48 connected to the base body 12. The cover 38 of the second exemplary embodiment of FIG. 6 corresponds to the cover 38 of the first exemplary embodiment of FIGS. 4 and 5. However, the bottom plates of these two exemplary embodiments differ. In contrast to the bottom plate 40 of the first exemplary embodiment, the bottom plate 48 of the second exemplary embodiment is designed in the form of a truncated cone. With the top surface of the truncated cone the bottom plate 48 adjoins the lower end face of the base body 12. As a result, the bottom plate 48 also serves as a foot of the fluidic device 10, which can support the base body 12 in a stable manner with respect to a subsurface. In the example shown, the top surface area of the truncated cone is slightly larger than the surface area of the adjacent end face of the base body 12. However, in alternative embodiments the top surface area of the truncated cone and the surface area of the adjacent end face of the base body 12 can correspond to one another.

Another difference between the bottom plate 40 of the first exemplary embodiment of FIGS. 4 and 5 and the bottom plate 48 of the second exemplary embodiment of FIG. 6 is that the bottom plate 48 comprises four channels 50 or grooves. The channels 50 are formed in the shell surface of the frustoconical bottom plate 48 and, in a state in which the bottom plate 48 is connected to the base body 12, are each arranged adjacent to one of the fluid outlets 26 of the fluid reservoirs 16. By means of the channels 50, fluid media emerging from the fluid outlets 26 can be discharged in a targeted manner into one or more adjacent collecting containers.

Figure 7A:
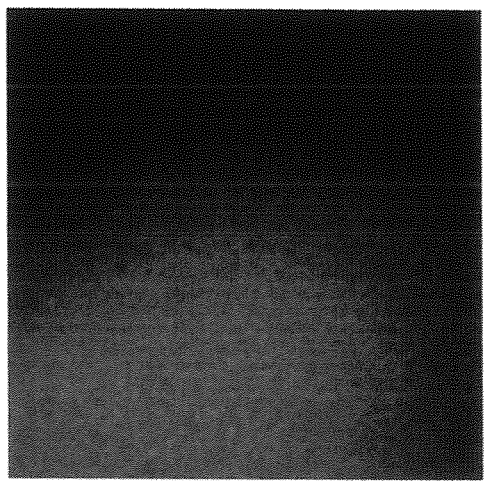
FIGS. 7A to 7C show an exemplary first concentration gradient at different points of the extension of a hydrogel matrix in the z-direction.
Figure 8A:
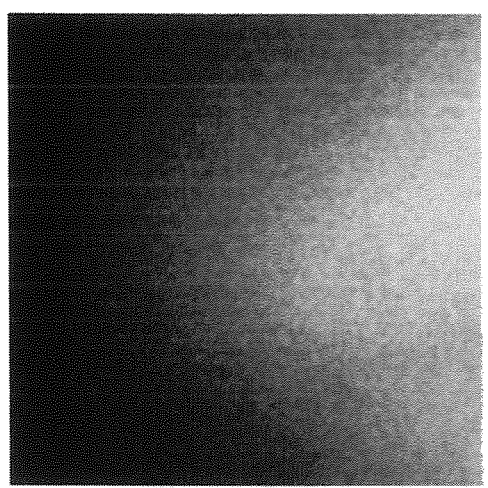
FIGS. 8A to 8C show an exemplary second concentration gradient at different points of the extension of a hydrogel matrix in the z-direction.
Figure 7B:
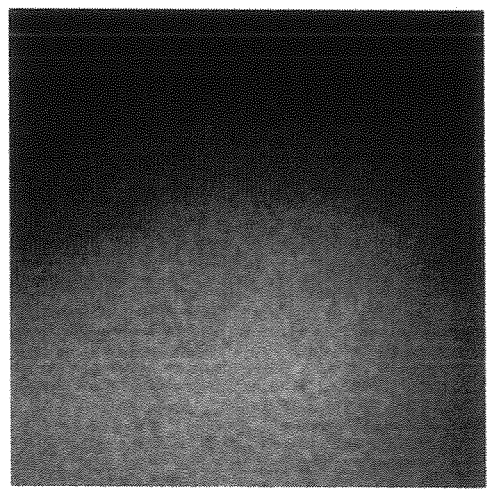
Figure 8B:
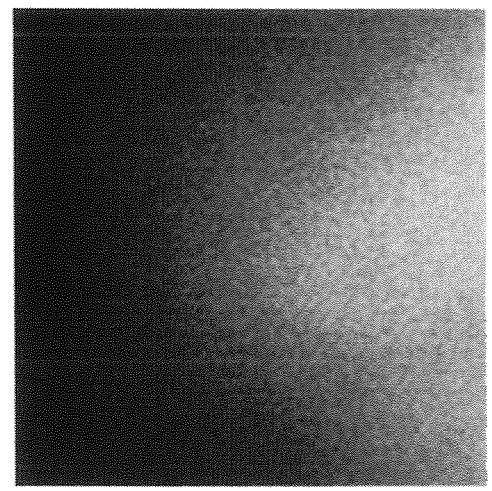
Figure 7C:
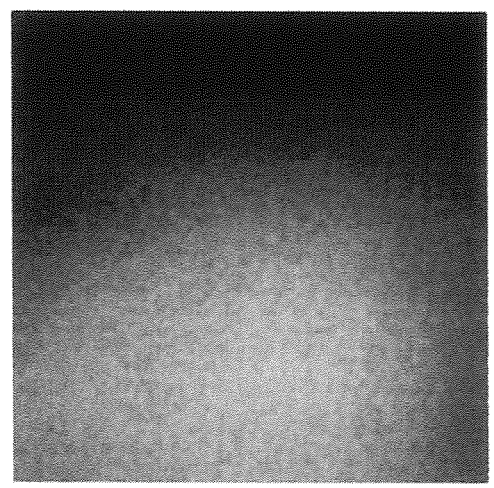
Figure 8C:
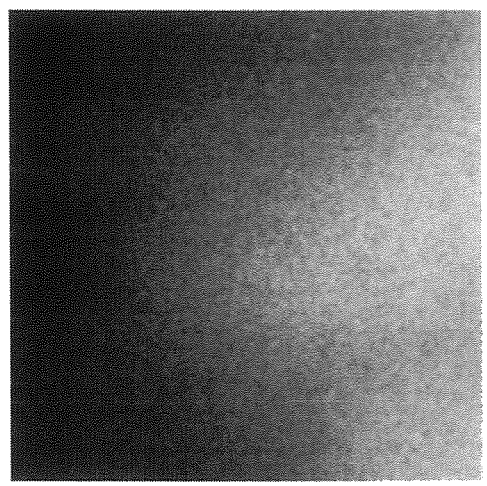

FIGS. 7A to 7C and 8A to 8C show an exemplary homogeneous concentration gradient that can be formed by means of the fluidic device 10 according to the invention at various points along the extension of the matrix in the z-direction. More precisely, FIGS. 7A and 8A each show a concentration gradient in the matrix at a distance of 1 mm from a lower end face of the chamber 14. FIGS. 7B and 8B each show a concentration gradient in the matrix at a distance of 2.5 mm from the lower end face of the chamber 14. FIGS. 7C and 8C each show a concentration gradient in the matrix at a distance of 4 mm from the lower end face of the chamber 14. FIGS. 7A to 7C show a concentration gradient that is formed in the matrix when using a fluid medium with Alexa fluor 647-Dextran in the fluid reservoir 16A (see FIG. 2) and a neutral fluid medium in the opposite fluid reservoir 16B (see FIG. 2), which have diffused into an agarose matrix via the associated separation devices 18A and 18B. FIGS. 8A to 8C show a concentration gradient that is formed in the hydrogel matrix when using a fluid medium with FITC-Dextran in the fluid reservoir 160 (see FIG. 2) and a neutral fluid medium in the opposite fluid reservoir 16D (see FIG. 2), which have diffused into an agarose matrix via the associated separating devices 18C and 18D. With the dyes used, the formation of two mutually orthogonal, homogeneous concentration gradients was shown as an example. In an analogous manner, biological substances (e.g. morphogens, substances that influence morphogenic signalling paths and/or differentiation paths, drugs) can be used for forming a concentration gradient.

LIST OF REFERENCE SYMBOLS 10 fluidic device
12 base body
14 chamber
16, 16A, 16B, 16C, 16D fluid reservoir
18, 18A, 18B, 18C, 18D separating device
20 through opening
22 shell
24 fluid inlet
26 fluid outlet
30 inlet opening
32 outlet opening
34 bore
36 end face
38 cover
40 bottom component
42 cover recess
44 bottom recess
46 bore
48 bottom component
50 channel
X1, X2 concentration gradient extending in the x-direction
Y1, Y2 concentration gradient extending in the y-direction

What is claimed is:

1. A fluidic device for developing a cellular starting material into a three-dimensional cellular structure, comprising a base body, including
    a chamber extending in an x-direction, a y-direction orthogonal to the x-direction and a z-direction orthogonal to the x-direction and the y-direction, in which a matrix is received, into which the cellular starting material to be developed can be is introduced; and
    at least two fluid reservoirs, wherein each of the at least two fluid reservoirs comprises:
    a fluid inlet for introducing a fluid medium into the fluid reservoir;
    a fluid outlet for discharging the fluid medium from the fluid reservoir; and
    a separating device which is partially permeable to the fluid medium and which separates one of the at least two fluid reservoirs from the chamber and forms a common plane interface between the one of the at least two fluid reservoirs and the chamber, via which the fluid medium diffuses into the matrix;

wherein the fluidic device is adapted, using fluid media, to form at least one concentration gradient, at least two mutually orthogonal concentration gradients and/or at least two mutually antiparallel concentration gradients (X1, X2, Y1, Y2) in the matrix which are each essentially homogeneous or deliberately inhomogeneous over at least a section of the extension of the matrix in the z-direction, the adaptation being effected by (i) two of the separating devices are present, with each extending in the z-direction and the x-direction and being arranged opposite to one another and being spaced from one another by the chamber in the y-direction; and/or (ii) two more of the separating devices are present, with each extending in the z-direction and the y-direction and being arranged opposite to one another and being spaced from one another by the chamber in the x-direction.

2. The fluidic device according to claim 1, wherein the chamber extends several hundred micrometers in the x-direction, in the y-direction and/or in the z-direction.

3. The fluidic device according to claim 1, wherein the chamber has a rectangular cross-section.

4. The fluidic device according to claim 1, wherein the separating devices are connected to one another and together form the chamber disposed between them.

5. The fluidic device according to claim 1, wherein each of the separating devices is designed in the form of a partition wall provided with a plurality of through openings.

6. The fluidic device according to claim 1, wherein the chamber comprises an inlet opening and an outlet opening, between which the chamber extends in the z-direction, so that the chamber can be transilluminated in the z-direction by means of optical beams.

7. The fluidic device according to claim 1, wherein the matrix is a hydrogel matrix or a basement membrane-like matrix.

8. The fluidic system for developing a cellular starting material into a three-dimensional cellular structure, comprising the fluidic device according to claim 1 and a pump system, wherein each fluid inlet is connected via an inlet hose to a pump for introducing a fluid medium into the fluid reservoir, wherein each fluid outlet is connected to an outlet hose for dis-charging the fluid medium from the fluid reservoir.

9. The fluidic device according to claim 2, wherein the chamber has a rectangular cross-section.

10. The fluidic device according to claim 1, wherein the chamber extends at least 1 mm in the x-direction, in the y-direction and/or in the z-direction.

11. The fluidic device according to claim 1, wherein the chamber extends several centimeters in the x-direction, in the y-direction and/or in the z-direction.

12. The fluidic device according to claim 1, wherein the chamber extends at least 10 cm in the x-direction, in the y-direction and/or in the z-direction.

13. The fluidic device according to claim 3, wherein the chamber has a square cross-section.

14. The fluidic device according to claim 1, wherein the matrix is an agarose matrix.

15. The fluidic system according to claim 8, wherein the pump is arranged to deliver the fluid medium at a flow rate between 1 and 1000 µl/h.

16. The fluidic system according to claim 8, wherein the pump is arranged to deliver the fluid medium at a flow rate between 1 and 100 µl/h through the fluid inlet.

17. The fluidic system according to claim 8, wherein the pump is arranged to deliver the fluid medium at a flow rate between 20 and 50 µl/h through the fluid inlet.

18. The fluidic system according to claim 8, wherein the outlet hose is connected to an outlet pump for applying a predetermined negative pressure to the fluid outlet.

19. A method for developing a cellular starting material into a three-dimensional cellular structure using the fluidic device according to claim 1, wherein the method comprises the steps:

providing the cellular starting material to be developed in the matrix which extends in the x-direction, the y-direction orthogonal to the x-direction and a z-direction orthogonal to the x-direction and the y-direction; and forming at least one concentration gradient, at least two mutually orthogonal con-centration gradients and/or at least two mutually antiparallel concentration gradients in the matrix, wherein each of the concentration gradients extends in the x-direction or in the y-direction and is a homogeneous or deliberately inhomogeneous concentration gradient in the z-direction.

20. A three-dimensional cellular structure, produced by the method according to claim 19.

* * * * *

UNITED STATES PATENT AND TRADEMARK OFFICE
CERTIFICATE OF CORRECTION

PATENT NO. : 12,252,677 B2
APPLICATION NO. : 17/287749
DATED : March 18, 2025
INVENTOR(S) : Ulrike Nuber et al.

Page 1 of 1

It is certified that error appears in the above-identified patent and that said Letters Patent is hereby corrected as shown below:

In the Claims

Column 18, Claim 1, Line 57: delete "can be"

Signed and Sealed this
Ninth Day of September, 2025

Coke Morgan Stewart
*Acting Director of the United States Patent and Trademark Office*